US008755909B2

(12) United States Patent
Sommer et al.

(10) Patent No.: US 8,755,909 B2
(45) Date of Patent: Jun. 17, 2014

(54) ACTIVE FIXATION MEDICAL ELECTRICAL LEAD

(71) Applicant: Medtronic, Inc., Minneapolis, MN (US)

(72) Inventors: John L Sommer, Coon Rapids, MN (US); Gareth Morgan, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/793,622

(22) Filed: Mar. 11, 2013

(65) Prior Publication Data
US 2013/0325094 A1 Dec. 5, 2013

Related U.S. Application Data

(60) Provisional application No. 61/654,348, filed on Jun. 1, 2012.

(51) Int. Cl.
*A61N 1/00* (2006.01)
*A61N 1/05* (2006.01)

(52) U.S. Cl.
CPC .................................. *A61N 1/0573* (2013.01)
USPC ........................................................ 607/127

(58) Field of Classification Search
CPC ..... A61N 1/0573; A61N 1/0563; A61N 1/05; A61N 1/057; A61N 2001/0578; A61N 2001/0585; A61M 2039/0223; A61M 2039/0232

USPC ........................................ 607/126–131, 9, 117
See application file for complete search history.

(56) References Cited

U.S. PATENT DOCUMENTS

| 5,443,492 | A | 8/1995 | Stokes et al. |
|---|---|---|---|
| 5,575,814 | A | 11/1996 | Giele et al. |
| 6,493,591 | B1 * | 12/2002 | Stokes ........................... 607/127 |
| 6,556,874 | B2 | 4/2003 | Audoglio |
| 6,943,591 | B1 | 9/2005 | Hannan et al. |
| 7,313,445 | B2 | 12/2007 | McVenes et al. |
| 7,529,584 | B2 * | 5/2009 | Laske et al. ....................... 607/9 |
| 7,532,939 | B2 | 5/2009 | Sommer et al. |
| 7,860,580 | B2 | 12/2010 | Falk et al. |
| 2008/0109042 | A1 | 5/2008 | Bodner et al. |
| 2008/0319520 | A1 | 12/2008 | Hill |

OTHER PUBLICATIONS (PCT/US2013/043620) PCT Notification of Transmittal of the International Search Report and the Written Opinion of the International Searching Authority.

* cited by examiner

*Primary Examiner* — Rex R Holmes
(74) *Attorney, Agent, or Firm* — Reed A. Duthler

(57) ABSTRACT

A medical electrical lead having an elongated lead body and a fixation helix extending along a generally helical axis, mounted around the outer circumference of the lead body. The fixation helix has a free end spaced from and extending from the lead body for less than the circumference of the lead body. The lead body includes an additional component which provides a rotation stop extending from the outer circumference of the lead body and provides stop surface generally perpendicular to the axis of the helix.

12 Claims, 12 Drawing Sheets

ACTIVE FIXATION MEDICAL ELECTRICAL LEAD

CROSS-REFERENCE TO RELATED APPLICATIONS

This application claims the benefit of U.S. Provisional Application No. 61/654,348, filed on Jun. 1, 2012. The disclosure of the above application is incorporated herein by reference in its entirety.

TECHNICAL FIELD

The present invention pertains to medical electrical leads and more particularly to implantable medical electrical leads including active fixation elements.

BACKGROUND

Implantable medical devices, for example cardiac pacemakers and defibrillators, often include elongate medical electrical leads having one or more electrodes to sense electrical activity and deliver therapeutic stimulation. In recent years, with the advent of left ventricular pacing to alleviate heart failure, leads have been advanced into the coronary veins in order to position the electrodes of the leads at left ventricular pacing sites, typically located in proximity to the base of the left ventricle. Although a variety of left ventricular pacing leads, along with methods for implanting such leads, have been developed, there is still a need for a lead including features that facilitate delivery to, and fixation at, sites in the coronary vasculature.

One type of left lead adapted for placement in the coronary vasculature is that disclosed in U.S. Pat. No. 7,860,580, issued to Sommer, et al. and incorporated herein by reference in its entirety. Another type of left lead adapted for placement in the coronary vasculature is that disclosed in U.S. Pat. No. 7,532,939, issued to Sommer, et al. and also incorporated herein by reference in its entirety.

Additional designs for a side-helix leads are disclosed in U.S. Pat. No. 5,443,492, issued to Stokes, et al. U.S. Pat. No. 7,529,584, issued to Laske, et al, U.S. Pat. No. 7,313,445, issued to McVenes, et al., U.S. Pat. No. 6,493,591, issued to Stokes, U.S. Pat. No. 6,556,874, issued to Audoglio., all of which are incorporated herein in their entireties.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

SUMMARY OF THE INVENTION

The present invention may comprise an improvement to the prior art leads as illustrated herein, which correspond to those disclosed in U.S. Pat. No. 7,860,580, cited above. FIGS. 1-6 are taken from this prior patent. Similarly, the present invention may comprise an improvement to the prior art leads as disclosed in U.S. Pat. No. 7,860,580, cited above or may comprise an improvement to any of the other prior art leads disclosed in the patents cited above of the same general type, including fixation mechanisms taking the form of a hook or coil extending from the lead body.

The invention comprises a mechanism for limiting the degree to which tissue can become wedged between the fixation mechanism and the lead body. The inventors have determined that such wedging can interfere with removal of the lead.

A lead according to the present invention includes an additional component to accomplish the desired result. The additional component is located adjacent the point at which the fixation mechanism extends from the lead body and in conjunction with the fixation mechanism and lead body defines a relatively blunt-ended recess. When the fixation mechanism is inserted into body tissue, the additional component serves to limit the extent to which the fixation mechanism penetrates the tissue and additionally limit the degree to into which the tissue is compressed between the fixation mechanism and the lead body. This in turn, prevents wedging of the tissue between the fixation mechanism and the lead body and facilitates removal of the lead without damage to the body tissue.

In a preferred embodiment, the assembly comprising the helix and the additional component together provide a fixation helix like that of the above-cited Stokes, et al. '492 patent that extends from the lead body for less than one full turn around the lead body. Preferably, the helix extends from around one half to three quarters of the circumference of the lead body.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Constructions, materials, dimensions, and manufacturing processes suitable for making embodiments of the present are known to those of skill in the field of the invention.

Figure 1:
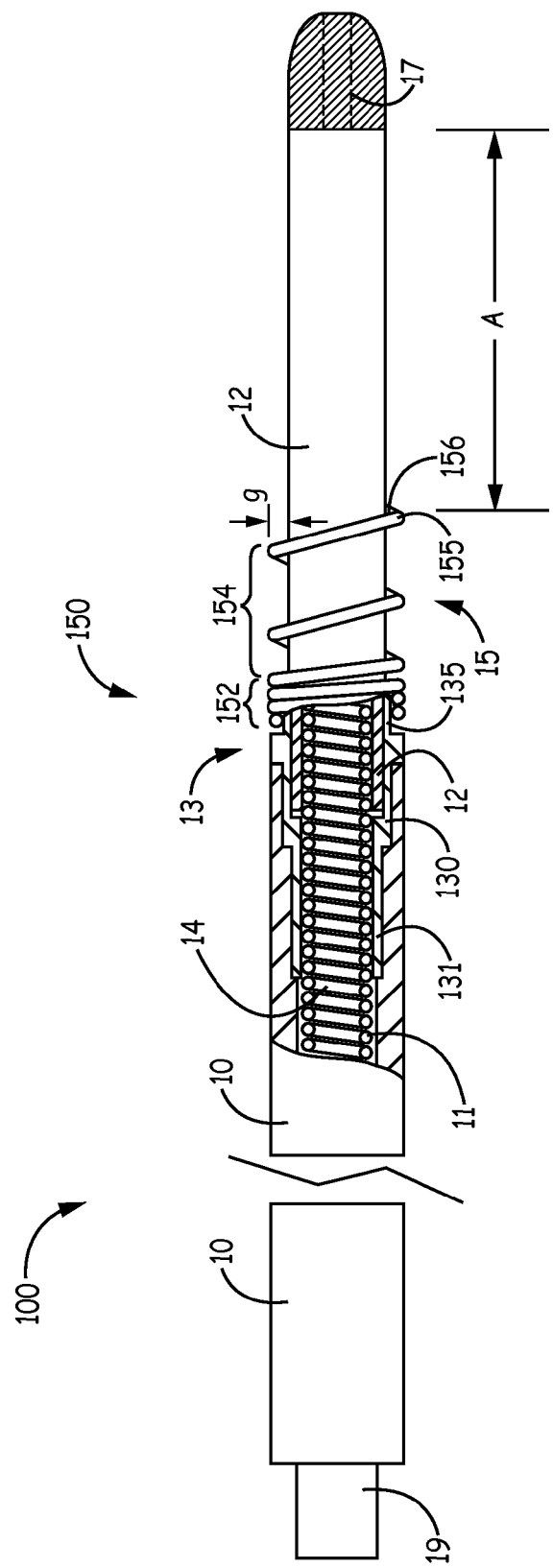
FIG. 1 is a plan view, including a partial section, of an electrical lead, according to the prior art.

FIG. 1 is a plan view, including a partial section, of an electrical lead 100, according to the prior art, to which the present invention may be added. FIG. 1 illustrates lead 100 including a proximal connector pin 19, a distal tip electrode 17, and an elongate conductor 11, for example, a multi-filar coil formed from MP35N alloy, which couples connector pin 19 to electrode 17. Connector pin 19 may be plugged into a port of an implantable medical device, for example a pacemaker, for electrical coupling, so that the device may send and receive electrical signals via conductor 11 and electrode 17; such a connection is well known to those skilled in the art. According to the illustrated embodiment, conductor 11 extends within a proximal insulation segment 10 and a distal insulation segment 12; proximal segment 10 generally defines a proximal portion of lead 100 and extends distally from connector pin 19; and, distal insulation segment 12 generally defines a distal portion of lead 100 and extends distally from a point in proximity to a distal end of proximal insulation segment 10 to electrode 17. Although conductor 11 is illustrated in the form of a coil, it should be noted that alternate forms of conductors, for example, cables, may be implemented within alternate embodiments of the present invention. The filars of coil 11 may each include an insulative coating to electrically isolate each filar from the other so coil 11 has the capacity to provide independent circuits for more than one electrode, for example as described below.

FIG. 1 further illustrates a fixation mechanism 150 coupled to the distal end of proximal insulation segment 10 and including a wire, which may have a diameter of approximately 0.008 inch, wound in a helix 15, which includes a tight-wound portion 152 and a space-wound portion 154; helix 15 extends distally over distal insulation segment 12 and terminates in a distal end 155, which includes a piercing tip 156. According to the illustrated embodiment, fixation element 150 further includes a stud component 13 having a distal surface 135 on which tight wound portion 152 of helix 15 is mounted for coupling, for example, via crimping or welding, and first and second proximal surfaces 130 and 131, respectively, over which proximal insulation segment 10 extends. Proximal insulation segment 10 may be adhesively bonded to one or both of proximal surfaces 130, 131. Component 13 is made of a conductive material and helix 15 functions as a second electrode of lead 100, for example, being formed of a platinum iridium alloy, and being coupled to one or more filars of multi-filar conductor coil 11; the one or more filars may be terminated in proximity to component 13 and lifted away from the other filars to engage second proximal surface 131 of component 13 for electrical coupling thereto, according to methods known to those skilled in the art, for example, via crimping or welding. Helix 15, serving as an electrode, may be of the same polarity as, or opposite polarity to, electrode 17.

The general construction illustrated in FIG. 1 may be employed in conjunction with the additional component as discussed below to provide a lead according to the present invention.

Figure 2A:
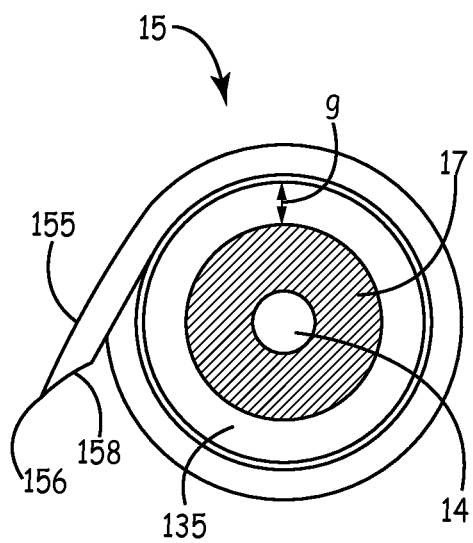
FIG. 2A is an end view of the lead shown in FIG. 1, according to one embodiment.
Figure 2B:
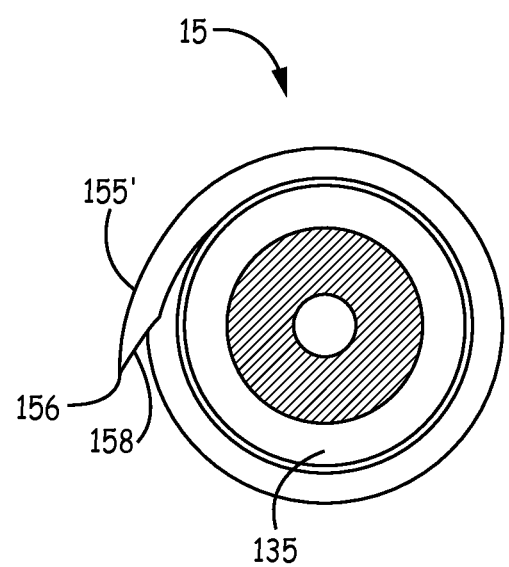
FIG. 2B is an end view of the lead shown in FIG. 1, according to an alternate embodiment.

FIG. 2A is an end view of lead 100, wherein piercing distal tip 156, according to one embodiment, is seen more clearly. FIG. 2A illustrates distal end 155 of helix 15 including a relatively flat surface 158, which may have been formed by grinding distal end 155, tapering from an inner side to an outer side of distal end 155 to form tip 156. FIG. 2A further illustrates helix distal end 155 offset, or angled outward, away from a centerline of helix 15, extending approximately tangent to a circle defined by helix 15. FIG. 2B is an end view of lead 100, according to an alternate embodiment, wherein a distal end 155' of helix 15, instead of extending tangent to a circle defined by helix 15, extends away from the circle in an eccentric path.

The general constructions illustrated in FIGS. 2A and 2B may be employed in conjunction with the additional component as discussed below to provide a lead according to the present invention.

Figure 3A:
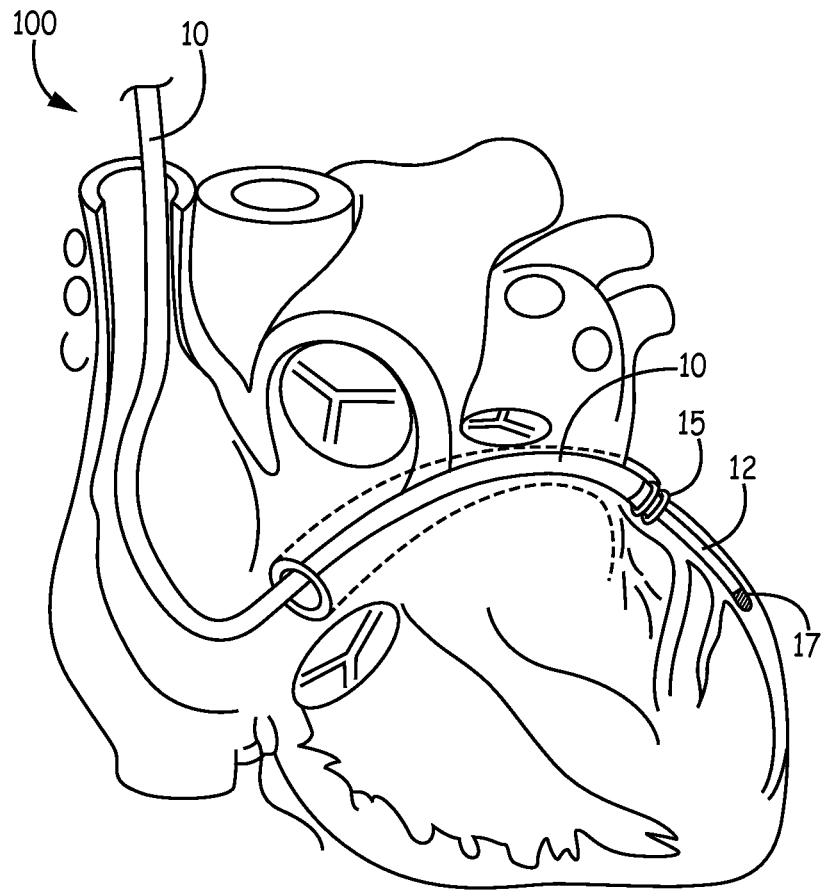
FIG. 3A is a schematic of an implanted lead as shown in FIG. 1.
Figure 3B:
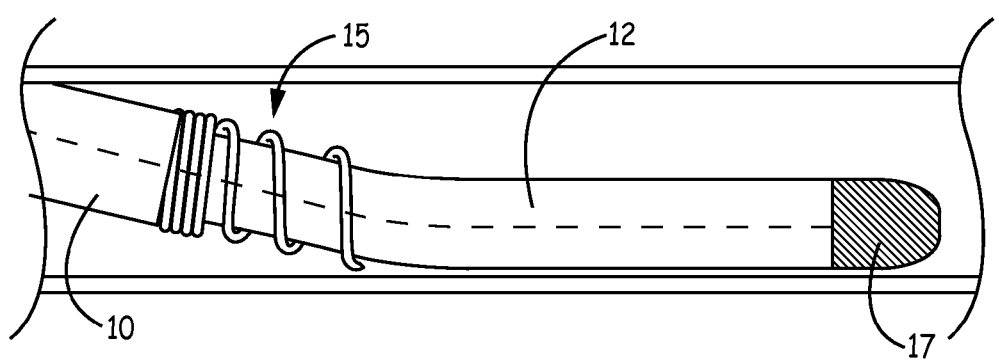
FIG. 3B is a schematic of a lead according to FIG. 1, directed for fixation.

Lead 100 may be implanted by fixing within a coronary vein, for example, to provide left ventricular pacing via electrode 17, by applying a rotational force to lead 100, in proximity to connector pin 19, which turns helix 15 so that piercing tip 156 engages and rotates through a wall of the coronary vein. With reference to FIGS. 1, 2 and 3A, it may be appreciated that lead 100 may be delivered to an implant site, as depicted in FIG. 3, with assistance from a stylet or guide wire inserted within a lumen 14 formed by coil conductor 11, according to methods well known to those skilled in the art. According to the illustrated embodiment, lumen 14 extends distally through electrode tip 17, thereby facilitating passage of a guide wire, which may be advanced ahead of tip 17. The portion of lumen 14 extending within tip electrode 17 may include a seal which allows passage of a guide wire but prevents ingress of bodily fluids into lumen 14; an example of a suitable seal is described in commonly assigned U.S. Pat. No. 6,192,280, salient portions of which are hereby incorporated by reference. Engaging a curved distal portion of a stylet within lumen 14, in proximity to fixation element 150, may further facilitate engagement of helix tip 156 with a vessel wall, by deflecting the distal portion of lead 100 away from tip 156, for example, as illustrated in FIG. 3B, wherein the dashed line represents the stylet. A lead incorporating the present invention may be implanted in the same manner as described above.

Referring now to FIG. 1, in conjunction with FIG. 3A, it should be noted that a distance A between helix distal end or tip 156 and electrode 17 should be sufficient at least to allow bending of the distal portion of lead 100 into branch vessels of the venous anatomy so that helix 15 may be fixed in a more proximal larger vein while still allowing electrode 17 to be positioned deep enough within a tributary branching off that larger vein. Furthermore, an outer diameter of helix 15, as defined by tight wound portion 152 and space wound portion 154, is shown to be approximately equal to an outer diameter of proximal insulation segment 10, which may further facilitate smooth advancement of lead 100 within the coronary anatomy and/or a guiding catheter, which may also be used to implant lead 100.

The general structural relationships discussed above may be employed in conjunction with the additional component as discussed below to provide a lead according to the present invention.

Figure 4:
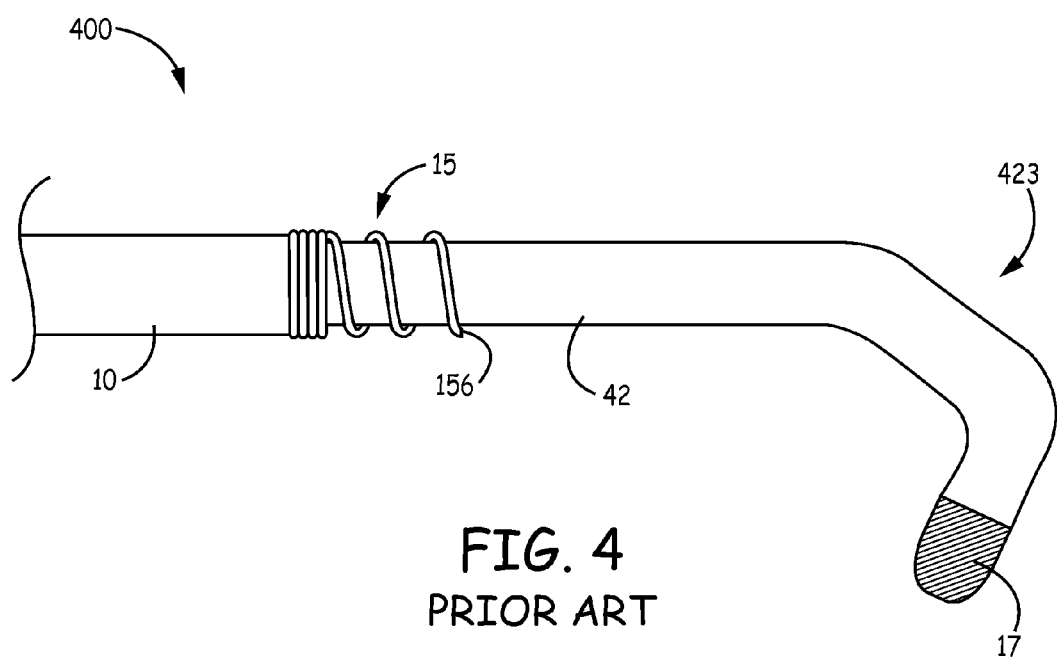
FIG. 4 is a plan view of an electrical lead, according to an alternate embodiment of the prior art.

FIG. 4 is a plan view of an electrical lead 400, according to an alternate embodiment of the prior art. FIG. 4 illustrates lead 400 including a distal insulation segment 42, generally defining a distal portion of lead 400, having a pre-formed curve 423 formed therein, according to methods known to those skilled in the art, for example, via molding or secondary heat forming; lead 400 is similar to lead 100 in other respects, for example, including proximal insulation segment 10, helix 15 and electrode tip 17. Pre-formed curve 423 may facilitate steering of lead 400 to a target site in the coronary vasculature and/or improve contact of electrode 17 with myocardial tissue.

The general construction illustrated in FIG. 4 may also be employed in conjunction with the additional component as discussed below to provide a lead according to the present invention.

Figure 5:
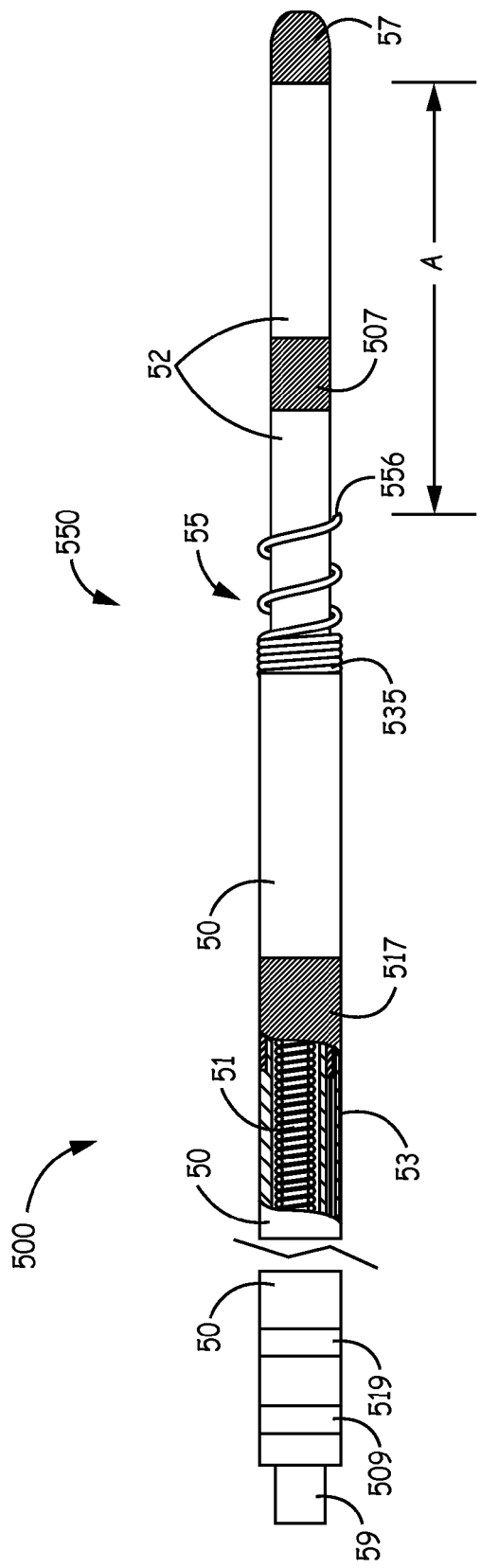
FIG. 5 is a plan view, including a partial section, of an electrical lead, to an alternate embodiment of the prior art.

FIG. 5 is a plan view, including a partial section, of an electrical lead 500, according to an additional alternative embodiment of the prior art. FIG. 5 illustrates lead 500 including a first conductor 51, for example, a multi-filar coil, and a second conductor 53, for example, a cable, isolated from one another and extending side-by-side within respective lumens of a proximal insulation segment 50, which generally defines a proximal portion of lead 500; first conductor 51 further extends into a distal insulation segment 52, which generally defines a distal portion of lead 500. According to the illustrated embodiment, conductor 51 electrically couples a first electrode 57 to a connector pin 59 and a second electrode 507 to a first connector ring 509; and conductor 53 couples a third electrode 517 to a second connector ring 519. Connector pin 59 and rings 509, 519 are part of a connector that terminates a proximal end of lead 500 and may be coupled to an implantable device such that each of electrodes 507 and 57 function to pace and/or sense and electrode 517 to sense or defibrillate, according to any system configuration known to those skilled in the art.

Figure 6:
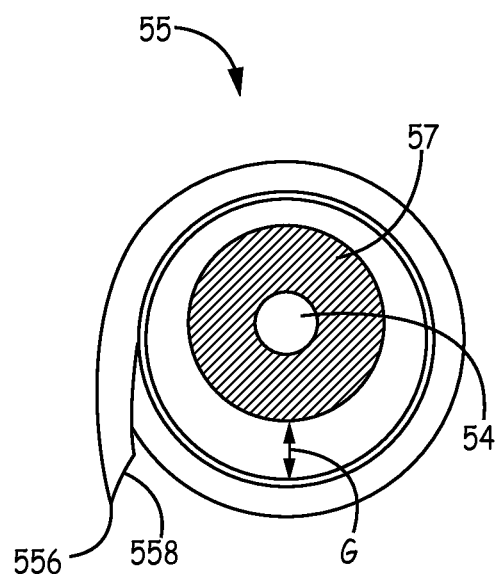
FIG. 6 is an end view of the lead shown in FIG. 5.

FIG. 5 further illustrates a fixation element 550 including a wire forming a helix 55, which is coupled to a distal end of proximal insulation element 50 and extends distally over distal insulation segment 52; element 550 may be coupled to the distal end in a manner similar to that described for fixation element 150 of lead 100. Helix 55 is shown including a piercing distal tip 556, which is spaced proximally from electrode 57 distance A as previously described for lead 100, and, similar to tip 156 of helix 15, for example, as illustrated in FIG. 6, including a relatively flat surface 558 tapering from an inner side to an outer side of helix 55. FIG. 6 is an end view of the lead shown in FIG. 5. It may be appreciated with reference to FIGS. 5 and 6 that lead 500 includes a lumen 54 extending within coil 51 and out through tip electrode 57. According to the illustrated embodiment, to accommodate conductor 53 alongside conductor coil 51, lumen 54 is offset such that distal insulation segment 52 is offset from a centerline of helix 55. Such an offset creates a gap G between helix 55 and distal segment 52, which is larger than a gap which would be created with a concentric distal segment, for example gap g shown in FIG. 2A; this larger gap G may further facilitate the engagement of helix tip 556 with a vessel wall as previously described.

Lead 500 may further include a fourth electrode 577, as illustrated in FIG. 7, which is disposed proximal to helix 55 and distal to third electrode 517. FIG. 7 is a schematic showing lead 500 implanted such that electrodes 517 and 577 are disposed in the coronary sinus to sense atrial activity, and electrodes 507 and 57 are disposed in a tributary of the great cardiac vein to pace and sense the left ventricle. It should be noted that electrode 517 may further serve as a defibrillation electrode.

The general construction illustrated in FIG. 5 may also be employed in conjunction with the additional component as discussed below to provide a lead according to the present invention.

Figure 6A:
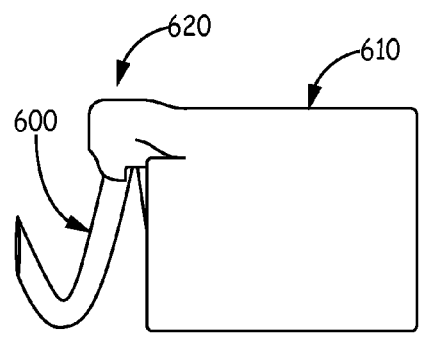
FIGS. 6A-C are plan side and end views of the views of the assembly comprising the helix and the additional component in a preferred embodiment.
Figure 6C:
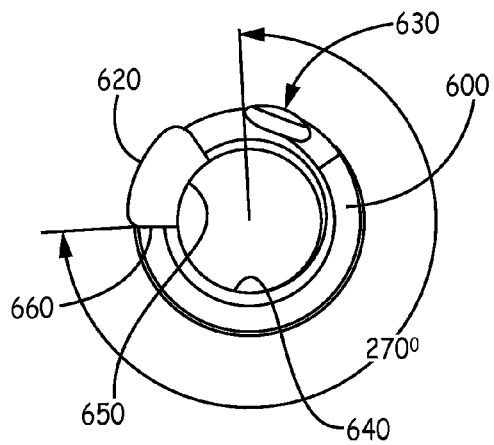
Figure 6B:
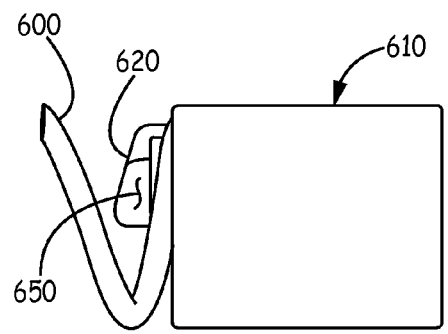

FIGS. 6A-C are plan side and end views of the views of the assembly comprising the helix 600 and the additional component 610, in a preferred embodiment. Component 610 is a generally cylindrical molded plastic part which encloses the majority of helix 600 and which is provided with a rotation stop 620, which includes a stop surface 660, generally perpendicular to the axis of the helix 600 and extending from the exterior surface of the lead body. Component 610 may be injection molded, for example, from 55D or 80A durometer polyurethane. In these views, it can be seen that at the point that helix 600 extends circumferentially from the stop surface 660, it is spaced radially outward from the outer surface body of the lead to which the assembly is mounted, illustrated schematically at 640. This relationship prevents tissue from wedging between the helix and the lead body to a degree that it would interfere with rotation of the helix to release it from the tissue if repositioning becomes necessary. The inner surface 650 of the rotation stop 620 is located against the outer surface of the lead body illustrated schematically at 640, also preventing wedging of the tissue between the rotation stop and the lead body The assembly as illustrated can be coupled to a conductor within the lead body, for example as illustrated in FIG. 1 or may be simply mounted around the insulative lead body. In the case in which the assembly is coupled to the conductor as in FIG. 1, it may be coupled, for example, by welding or mechanically coupling the helix to component 130 (FIG. 1) or t a similar component. In alternative embodiments, the helix may simply take the form of an exposed distal portion of the conductor 11 (FIG. 1). In such embodiments, the additional component 610 preferably encloses the proximal portion of the Helix 600 and thus defines an available fixation helix which extend only partially around the circumference of lead body 12 (FIG. 1).

In the case in which the assembly of the helix 600 and the additional component 610 are mounted to the lead body, unconnected to any lead conductors, the assembly may simply be adhesively or mechanically coupled to an outer surface of the lead body, for example to the outer surface of lead body component 10 or component 12 (FIG. 1). As discussed below, in such embodiments, additional refinements to the design of the coil 600 may be employed to enhance the mounting of the assembly to the lead body.

Figure 7A:
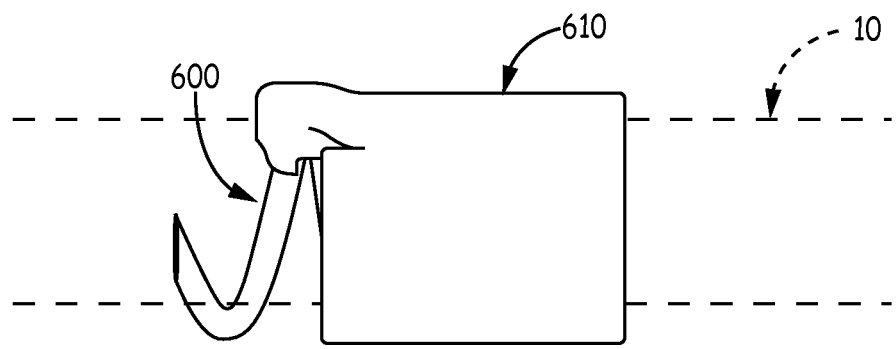
FIGS. 7A and 7B illustrate schematically the relationship between the assembly of FIGS. 6A-C and lead body of FIG. 1.
Figure 7B:
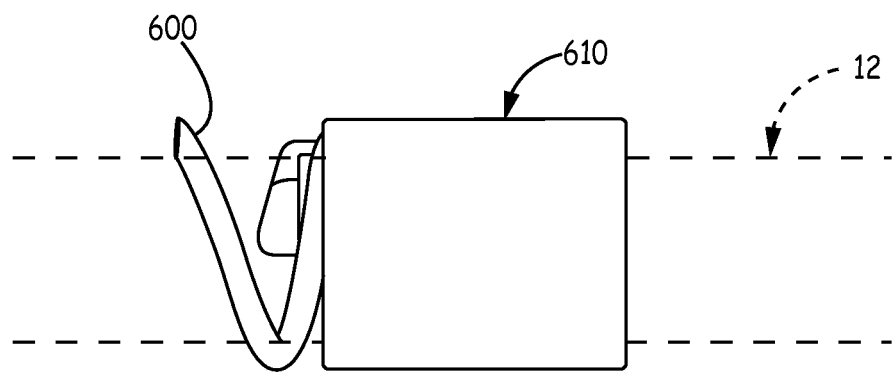

FIGS. 7A and 7B illustrate schematically the relationship between the assembly of FIGS. 6A-C and lead body component 10 or 12 of FIG. 1 as illustrated in broken line outline. In these views, it can be seen that the helix 600 extends from the additional component 610 spaced radially outward of the lead body for less than one full turn, corresponding in this manner to the helix of the above-cited Stokes, et al. '492 patent. However, unlike the Stokes, et al. design, the additional component provides reinforcement to the helix at the point it exits component 610, reducing the likelihood that over-torqueing of the lead will result in bending the helix outward and possibly resulting either unintended tissue damage or interference with reliable fixation.

Figure 8B:
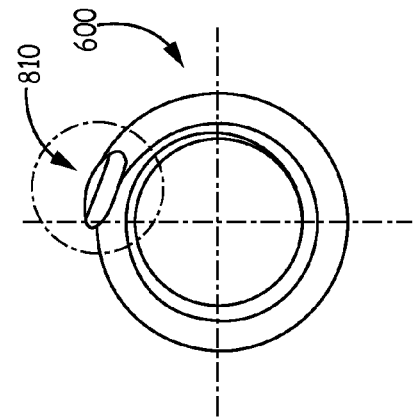
FIGS. 8A-E are illustrations of details of construction of the helix.
Figure 8E:
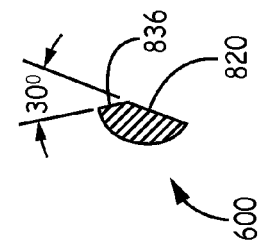
Figure 8D:
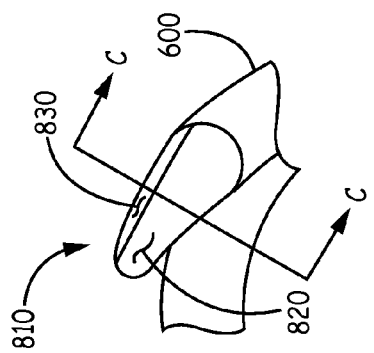
Figure 8A:
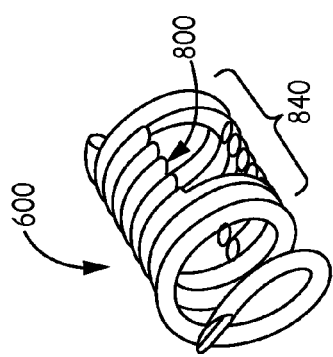

FIGS. 8A-E are illustrations of details of construction of helix 600. In FIG. 8A, an embodiment of the helix is illustrated in which the proximal coils extending along length 840 are welded to one another to provide a rigid cylindrical structure. Windows 800 are laser cut into the welded coils on opposite sides of the helix 600. These windows provide a volume in which adhesive can be located, adhesively and mechanically coupling the assembly to a lead body. These windows are believed especially useful in embodiments in which the helix is mounted directly to the insulative lead body and is not welded to a conductor or other component of the lead. However, the windows may also be employed in other embodiments.

FIG. 8B shows the helix from an end view, more clearly illustrating the beveled tip 801 which penetrates body tissue. Like the heilx in the above-cited Sommer, et al. '580 patent, the distal portion of the helix extends radially outward from the more proximal portion. to assist in penetration of tissue during rotation of the lead body. FIG. 8B also illustrates the beveled tip 810 of the helix which, like that of the cited Sommer '850 Patent, provides a piercing tip having a relatively flat surface tapering from an inner side of the helix to an outer side of the helix to form the piercing tip. However, in the illustrated embodiment, the relatively flat surface comprises two surfaces angled to one another as illustrated in FIGS. 8C-E.

Figure 8C:
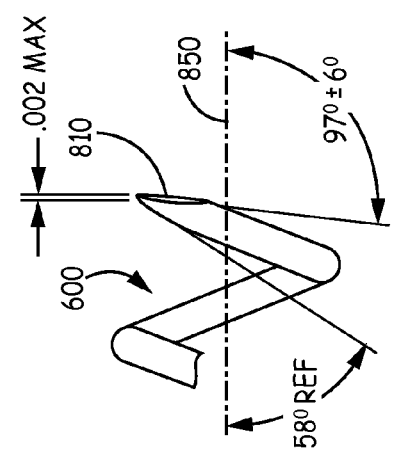

In FIGS. 8C-E it can be seen that beveled tip 810 comprises a major surface 820, located in a plane roughly 97 degrees to the axis of the lead body, (schematically illustrated at 850) and a minor surface 836, angled back approximately 30 degrees from the major surface 820. This configuration is believed to be especially useful in facilitating controlled penetration of the body tissue during rotation of the lead body.

Figure 9A:
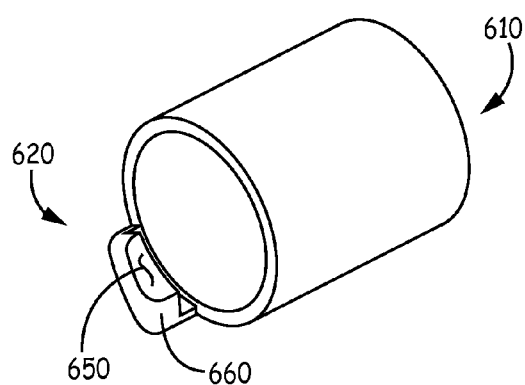
FIGS. 9A-C are illustrations of details of construction of the additional component.
Figure 9B:
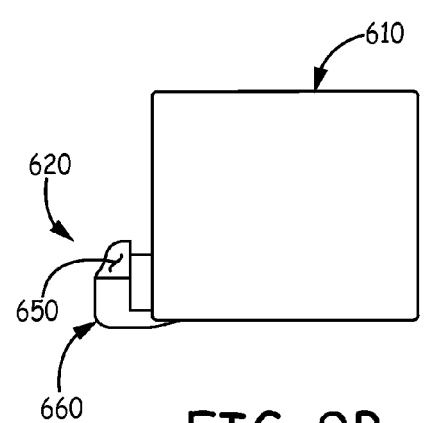
Figure 9C:
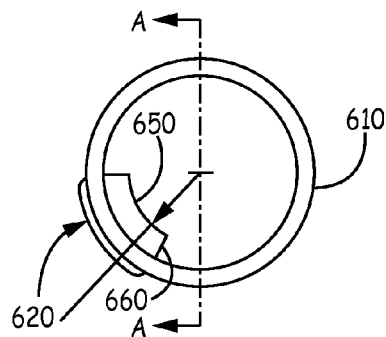

FIGS. 9A-C are illustrations of details of construction of the additional component 610.

In the foregoing detailed description, the invention has been described with reference to specific embodiments. However, it may be appreciated that various modifications and changes can be made without departing from the scope of the invention as set forth in the appended claims.

The invention claimed is:

1. A medical electrical lead, comprising:
an elongated lead body having an outer circumference;
a fixation helix extending along a generally helical axis, mounted around the outer circumference of the lead body, the fixation helix comprising a free end spaced from and extending from the lead body for less than the circumference of the lead body; and
wherein the lead body comprises an additional component which provides a rotation stop extending from the outer circumference of the lead body and comprising a stop surface generally perpendicular to the axis of the helix;
wherein the lead body comprises a cylindrical lead body component and wherein the additional component is a plastic component attached to an outer surface of the cylindrical lead body component.

2. A lead according to claim 1 wherein the plastic component is a molded plastic component, separately molded from the cylindrical lead body component.

3. A medical electrical lead, comprising:
an elongated lead body having an outer circumference;
a fixation helix extending along a generally helical axis, mounted around the outer circumference of the lead body, the fixation helix comprising a free end spaced from and extending from the lead body for less than the circumference of the lead body; and
wherein the lead body comprises an additional component which provides a rotation stop extending from the outer circumference of the lead body and comprising a stop surface generally perpendicular to the axis of the helix;
wherein proximal coils of the helix are welded to one another and wherein the fixation helix is provided with a window extending through the proximal coils.

4. A lead according to claim 1 wherein the additional component encloses proximal coils of the helix.

5. A lead according to claim 1 wherein the lead comprises an electrode mounted to the lead body.

6. A lead according to claim 5 wherein the electrode is mounted to the lead body distal to the helix.

7. A lead according to claim 3 wherein the additional component encloses proximal coils of the helix.

8. A lead according to claim 3 wherein the lead comprises an electrode mounted to the lead body.

9. A lead according to claim 8 wherein the electrode is mounted to the lead body distal to the helix.

10. A medical electrical lead, comprising:
an elongated lead body having an outer circumference;
a fixation helix extending along a generally helical axis, mounted around the outer circumference of the lead body, the fixation helix comprising a free end spaced from and extending from the lead body; and
wherein the lead body comprises an additional component which provides a rotation stop extending from the outer circumference of the lead body and comprising a stop surface generally perpendicular to the axis of the helix;
wherein the lead body comprises a cylindrical lead body component and wherein the additional component is attached to an outer surface of the cylindrical lead body component and encloses proximal coils of the helix.

11. A lead according to claim 10 wherein the lead comprises an electrode mounted to the lead body.

12. A lead according to claim 11 wherein the electrode is mounted to the lead body distal to the helix.

* * * * *